United States Patent [19]

Sherman

[11] Patent Number: 5,843,891
[45] Date of Patent: Dec. 1, 1998

[54] PHARMACEUTICAL ACCEPTABLE COMPOSITIONS CONTAINING AN ALCOHOL AND A HYDROPHOBIC DRUG

[76] Inventor: Bernard C. Sherman, 50 Oldcolony Road, Willowdale, Ontario, Canada, M2L 2K1

[21] Appl. No.: 537,697

[22] PCT Filed: Apr. 22, 1994

[86] PCT No.: PCT/CA94/00222

§ 371 Date: Oct. 27, 1995

§ 102(e) Date: Oct. 27, 1995

[87] PCT Pub. No.: WO94/25068

PCT Pub. Date: Nov. 10, 1994

[30] Foreign Application Priority Data

Apr. 28, 1993 [NZ] New Zealand ............................ 247516

[51] Int. Cl.⁶ ..................................................... A61K 38/13
[52] U.S. Cl. ................................................................. 514/11
[58] Field of Search ................................................... 514/11

[56] References Cited

U.S. PATENT DOCUMENTS 4,388,307  6/1983  Cavanak ................................. 424/177

FOREIGN PATENT DOCUMENTS

| 0294239 | 7/1988 | European Pat. Off. . |
| 64-38029 | 2/1989 | Japan . |
| 2222770 | 3/1990 | United Kingdom . |
| 2 228 198 | 8/1990 | United Kingdom . |

OTHER PUBLICATIONS

Physicians' Deck Reference, 46$^{th}$ ed. (1992) pp. 2024–2027.

*Primary Examiner*—Phyllis G. Spivack
*Attorney, Agent, or Firm*—Nixon & Vanderhye P.C.

[57] ABSTRACT

Pharmaceutical compositions having improved physical and absorption properties are disclosed, wherein a hydrophobic drug is dissolved in a solvent system comprising at least one alcohol having a boiling point above 100° C. and a solubility in water inferior to 10 g per 100 g at 20° C. and a surfactant.

17 Claims, No Drawings

PHARMACEUTICAL ACCEPTABLE COMPOSITIONS CONTAINING AN ALCOHOL AND A HYDROPHOBIC DRUG

This application is a 371 of PCT/CA94/00222 filed Apr. 22, 1994.

TECHNICAL FIELD

This invention is directed to pharmaceutical compositions which facilitate the in vivo absorption of hydrophobic drugs, including but not limited to polypeptide and protein drugs.

BACKGROUND ART

The hydrophobic nature of some drugs causes them to be insoluble or poorly soluble in aqueous media. This reduces the absorption of the drug into systemic circulation after a composition containing the drug is swallowed, or the absorption into the target tissues upon topical application.

Previous attempts to deal with this problem have included forming a solution, either liquid or solid, incorporating the drug, whereby the drug is disseminated as molecular size particles within the solvent. If the solvent is water-soluble, upon ingestion of the composition the solvent dissolves and releases the drug as individual molecules which are more readily available for absorption than larger particles would be.

Problems previously encountered with this approach include:

1) Low solubility of the drug in a pharmaceutically acceptable solvent may require large quantities of solvent. This limits the amount of the drug that can be contained in a tablet or capsule of acceptable, swallowable size;

2) The composition may not be sufficiently stable on storage, and as a consequence the drug is precipitated and the efficacy diminishes; and 3) Upon ingestion of the composition, as the solvent in the composition dissolves in the gastrointestinal fluids, the drug may precipitate and agglomerate into larger particles that are poorly absorbed.

Among the drugs that are hydrophobic and give rise to such problems are nonpolar polypeptides, including cyclosporins, as defined in the Merck Index, Eleventh Edition. One such cyclosporin is cyclosporin A, also known as cyclosporine, and hereinafter referred to as "cyclosporine", known to be therapeutically active as an immunosuppressant.

U.S. Pat. No. 4,388,307 discloses a composition comprising cyclosporine in an emulsion preconcentrate that is not water-soluble, but upon being mixed into gastrointestinal fluids forms an emulsion. The advantage of such compositions is that the cyclosporine in the emulsion is absorbed to a substantially greater extent than from other compositions previously known.

However, such compositions still suffer from certain disadvantages;

Although the absorption is superior to that of some compositions, the absorption is still less than the maximum possible and is variable.

Further, the concentration of cyclosporine in such compositions is limited to about 10 percent by weight. Hence, a capsule containing 100 mg of cyclosporine weighs about 1 gram. Capsule strengths are thus limited to about 100 mg, as higher strength capsules would be too large to be swallowed.

Others have attempted to solve the formulation problems by developing solutions of cyclosporine (either liquid or solid solutions) that are entirely water-soluble and form a clear solution upon being dispersed in aqueous media such as gastrointestinal fluids.

European Patent Application No. 88305138.5 discloses use of a surfactant or solubilizing agent which is alphacyclodextrin or a derivative thereof.

Other publications and patent applications disclose compositions comprising cyclosporine together with surfactants, which also form clear solutions upon their addition to aqueous media.

However, such compositions have been generally impractical, as the quantities of surfactant needed to render cyclosporine entirely water-soluble have been unacceptably large. Typical therapeutic doses of such compositions would require toxic quantities of the surfactants.

Others have provided compositions in which surfactants are used in quantities less than sufficient to entirely solubilize the cyclosporine in water. Japanese Patent No. 1038029 discloses preparation of powders by dissolving cyclosporine and surfactants in organic solvents and evaporating the solvents. However, the compositions described do not fully solubilize the cyclosporine, and organic solvents are costly and more difficult to use than water in the manufacturing process.

U.K. Patent Application No. 8920597.5 discloses "microemulsion preconcentrates" which are stated to be improved over compositions disclosed in U.S. Pat. No. 4,388,307. It is disclosed that a composition which, in addition to the active drug, comprises a hydrophilic phase, a lipophilic phase and a surfactant will, when added to water, disperse into an emulsion of smaller droplets than prior compositions, leading to superior absorption.

However, these formulations also have several limitations including:

1) The need to use several inactive ingredients;

2) The concentration of active drug that can be achieved is limited to about 15% in practice;

3) The ingredients that must be used and the quantities required may give rise to concerns about toxicity of the inactive ingredients; and 4) The absorption that can be achieved with practical formulations may still be less than optimum.

The emulsion preconcentrates disclosed in both U.S. Pat. No. 4,388,307 and U.K. Patent Application No. 8920597.5 have the feature that they have a hydrophilic phase which is the primary solvent for the active drug. In U.S. Pat. No. 4,388,307 the hydrophilic solvent is ethanol, and in British Application No. 8920597.5 other hydrophilic solvents are used such as Glycofurol 75, Transcutol, and Propylene Glycol.

The use of such hydrophilic solvents in emulsion preconcentrates is a cause of some of the limitations of such compositions disclosed in the prior art.

For example, when the emulsion preconcentrates are dispersed in water, some of the hydrophilic solvent can be drawn out of the emulsified phase and into solution in the water. Some of the active drug will be drawn along with the hydrophilic solvent and will precipitate as the solvent dissolves in the water. This precipitation reduces the quantity of the drug available for absorption.

Furthermore, the use of a hydrophilic phase also requires the use of a hydrophobic or lipophilic phase in the emulsion preconcentrate to enable the formation of an emulsion, thus increasing the total quantity of inactive ingredients required, and this in turn also requires an increased quantity of surfactant in the emulsion preconcentrates.

Furthermore, ethanol and other hydrophilic solvents previously used are relatively volatile and may evaporate from the composition on storage, resulting in precipitation of the drug. The compositions may thus have inadequate stability on storage unless specially packaged to prevent the evaporation.

The term "drug" as used herein and in the accompanying claims is to be understood as meaning any pharmacologically active compound useful for the treatment or prevention of disease in humans or animals, including but not limited to nonpolar peptides.

The term "composition" as used herein and in the accompanying claims is to be understood as meaning any composition containing a drug along with inactive ingredients that are pharmaceutically acceptable by reason of not being excessively toxic in the quantity required; e.g. where oral administration is intended, acceptable for oral use, and where topical administration is intended, for topical use.

DISCLOSURE OF THE INVENTION

The present invention is directed to pharmaceutical compositions which enable improved absorption of a hydrophobic drug while at the same time enabling the drug to be contained in the composition at relatively high concentrations.

In particular the present invention is directed to such compositions in the form of emulsions or emulsion preconcentrates, an emulsion preconcentrate being defined as a composition that, when added to water, readily disperses to form an emulsion.

An object of the invention is to eliminate the need to use a hydrophilic solvent as the primary solvent, in order to obviate the problems associated in the use of hydrophilic solvents as previously described.

For the purpose of this description, it will be understood that the term "solvent system" means the material in which the drug is dissolved. The solvent system may be a single solvent or a combination or mixture of ingredients included as solvents, surfactants, diluents, or for other purposes.

A primary feature of the invention is to use, as sole solvent or principal solvent in the solvent system, an alcohol that has a boiling point above 100° C., and that has a solubility in water of under 10 g per 100 g at 20° C. Such alcohols are less hydrophilic than ethanol or other solvents that have been previously used as the hydrophilic solvent in emulsion preconcentrates. Such alcohols will generally have 4 or more carbon atoms per molecule.

In view of the use of alcohols as solvent, it will be understood that the invention is applicable to drugs having adequate solubility in alcohols. Included among such drugs is cyclosporine.

Alcohols that may be used within the scope of the present invention may include any pharmaceutically acceptable alcohol having a boiling point above 100° C. and a solubility in water of under 10 g per 100 g at 20° C. Preferably, the alcohol will have a boiling point above 150° C., and a solubility in water of under 5 g per 100 g at 20° C. Preferably the alcohol will have 6 to 16 carbon atoms per molecule. The use of alcohols having greater than 16 carbon atoms is generally impractical as they generally have melting points above 40° C. Suitable alcohols include but are not limited to 1-hexyl, 1-octyl, 2-octyl, 1-decyl, 1-dodecyl, 1-tetradecyl, benzyl and phenethyl alcohols.

Generally, as the number of carbon atoms per molecule is increased, alcohols become less hydrophilic and more hydrophobic. For example, ethyl alcohol (having 2 carbon atoms) is infinitely soluble in water at 20° C. whereas 1-butyl alcohol, (having 4 carbon atoms) has a solubility of only 7.9 g per 100 g of water, 1-hexyl (having 6 carbon atoms) has a solubility of only 0.6 g per 100 g. 1-octyl alcohol (having 8 carbon atoms) has a solubility of only 0.05 g per 100 g. and 1-decyl alcohol (having 10 carbon atoms) is essentially insoluble.

In addition to being less hydrophilic and more hydrophobic, the alcohols having more carbon atoms per molecule generally have higher boiling points and are less volatile at ambient temperature, so that use of alcohols with more carbon atoms per molecule can eliminate the problem of volatility of the hydrophilic solvents encountered with prior-art compositions.

In some applications of the invention it may be useful to use a combination of two or more alcohols instead of one. One alcohol may be selected as being superior as a solvent for the drug and another may be selected as superior for ease of dispersion in water. A combination of the two may be better than either alone to enable higher concentration of the drug and adequate ease of dispersion.

Another feature of the present invention is that the solvent system in which the drug is dissolved, in addition to including at least one alcohol meeting the aforesaid requirements, will include at least one pharmaceutically acceptable surfactant, which serves to make the composition dispersible in water to form an emulsion.

Examples of suitable surfactant are:
(i) Reaction products of natural or hydrogenated vegetable oils and ethylene glycol; i.e., polyoxyethylene glycolated natural or hydrogenated vegetable oils; for example polyoxyethylene glycolated natural or hydrogenated castor oils. Particularly suitable are the products designated in the United States Pharmacopoeia and National Formulary as Polyoxyl 35 Castor Oil and Polyoxyl 40 Hydrogenated Castor Oil, which are available under the trade names Cremaphor EL and Cremaphor RH40 respectively. Also suitable for use in this category are the various tensides available under the trade name Nikkol, e.g. Nikkol HCO-60. The said product Nikkol HCO-60 is a reaction product of hydrogenated castor oil and ethylene oxide.
(ii) Polyoxyethylene-sorbitan-fatty acid esters; e.g. mono- and tri-lauryl, palmityl, stearyl and oleyl esters; e.g. products of the type known as polysorbates and commercially available under the trade name Tween.
(iii) Polyoxyethylene fatty acid esters; for example, polyoxyethylene stearic acid esters of the type known and commercially available under the trade name Myrj as well as polyoxyethylene fatty acid esters known and commercially available under the trade name Cetiol HE.
(iv) Polyoxyethylene-polyoxypropylene co-polymers, e.g. of the type known and commercially available under the trade names Pluronic and Emkalyx.
(v) Polyoxyethylene-polyoxypropylene block copolymers, e.g. of the type known and commercially available under the name Poloxamer.
(vi) Dioctylsuccinate,dioctylsodiumsulfosuccinate,di-[2-ethylhexyl]-succinate or sodium lauryl sulfate.
(vii) Phospholipids, in particular lecithins.
(viii) Propylene glycol mono- and di-fatty acid esters such as propylene glycol dicaprylate, propylene glycol dilaurate, propylene glycol hydroxystearate, propylene glycol isostearate, propylene glycol laurate, propylene glycol ricinoleate, propylene glycol sterate and so forth.
(ix) Bile salts; e.g. alkali metal salts, for example sodium taurocholate.

(x) Trans-esterification products of natural vegetable oil triglycerides and polyalkylene polyols; e.g. of the type known and commercially available under the trade name Labrafil M1944CS.

(xi) Mono-, di- and mono/di-glycerides, especially esterification products of caprylic or capric acid with glycerol.

(xii) Sorbitan fatty acid esters; for example, of the type known and commercially available under the trade name Span.

(xiii) Pentaerythritol fatty acid esters and polyalkylene glycol ethers; for example pentaerythritedioleate, -distearate, -monolaurate, polyglycol ether and -monostearate as well as pentaerythrite-fatty acid esters.

(xiv) Monoglycerides; e.g. glycerol monooleate, glycerol monopalmitate and glycerol monostearate; for example as known and commercially available under the trade names Myvatex, Myvaplex and Myverol, and acetylated, e.g. mono-and di-acetylated monoglycerides; for example as known and commercially available under the trade name Myvacet.

(xv) Glycerol triacetate or (1,2,3)-triacetin; and (xvi) Sterols and derivatives thereof, for example cholesterols and derivatives thereof, in particular phytosterols; e.g. products comprising sitosterol, campesterol or stigmasterol, and ethylene oxide adducts thereof, for example soya sterols and derivatives thereof, such as known under the trade name Generol.

Suitable surfactants will not be limited to those listed above, but will be understood to include any compound which causes the composition to be more easily dispersible in water.

When the surfactant also is an effective-solvent for the drug, it may be incorporated not only as surfactant, but as an additional carrier or co-solvent, to reduce the amount of alcohol required.

It will be understood that not all surfactants will act equally well with all alcohols to improve dispersion, and moreover, not all alcohols will work equally well as suitable solvents for all drugs. Determination of suitable combinations of alcohols and surfactants for particular applications within the scope of the invention will be within the capability of persons skilled in the art of product formulation.

Compositions in accordance with the invention may contain other ingredients in addition to the drug and one or more alcohols and one or more surfactants.

For example, the solvent system in which the drug is dissolved may include, in addition to one or more alcohols and one or more surfactants, one or more other ingredients that are interdissolved with the alcohol and surfactant and are included as co-solvents or diluents.

A composition in accordance with the invention may also contain, for example, a thickening agent (i.e., viscosity increasing agent). Suitable thickening agent (i.e., viscosity increasing agent). Suitable thickening agents may be of any of those known and employed in art, including, for example, pharmaceutically acceptable polymeric materials and inorganic thickening agents. However, where oral administration is intended, the use of thickening agents as aforesaid will generally not be required. Use of thickening agents is, on the other hand, indicated, e.g. where topical application is foreseen.

Compositions in accordance with the invention may also include one or more further ingredients; such as diluents, anti-oxidants, flavouring agents and so forth.

Compositions in accordance with the invention may be liquids at ambient temperatures or they may be solids prepared, for example, by use of alcohols or surfactants with melting points above ambient temperatures. The ingredients may be blended at temperatures above the melting point and then cooled to form solids. The solids may be ground into powder granules for further processing; for example, filling capsules or manufacture of tablets.

The capsules or tablets may be further processed by applying coatings thereto.

Especially where oral administration is contemplated, compositions in accordance with the invention may comprise end dosage forms for administration as emulsion preconcentrates. For example the emulsion preconcentrate may be directly used as liquid for oral ingestion, parenteral use, or topical application or it may be encapsulated into gelatin capsules for oral ingestion.

However, the present invention also provides pharmaceutical compositions in which the emulsion preconcentrate is further processed into an emulsion. Thus where oral administration is practiced, emulsions obtained, e.g. by diluting an emulsion preconcentrate with sufficient water or other aqueous medium (for example, a sweetened or flavoured preparation for drinking), may be employed as formulations for drinking. Similarly, where topical application is foreseen, compositions comprising an emulsion preconcentrate, a thickening agent, and water will provide an aqueous emulsion in gel, paste, cream or like form.

It should be noted that the droplet size of the emulsion formed when an emulsion preconcentrate according to the invention is dispersed in water will depend upon the identity and quantity of the ingredients used.

Generally, for a given composition, droplet size will decrease as the amount of surfactant is increased. Generally, smaller emulsion droplet size will enable improved absorption, so that there is usually an advantage to using more surfactant to obtain decreased droplet size. However, increased quantity of surfactant may also imply increased toxicity from the surfactant, increased cost and increased size of the dosage form of any desired strength. Moreover, if enough surfactant has been used to achieve absorption close to the maximum achievable, little is to be gained by adding more surfactant.

Hence, it will be understood that the quantity of the surfactant must be selected as sufficient to achieve maximum or near-maximum absorption without use of more than needed so as to avoid excessive toxicity, cost and dosage form size.

Compositions in accordance with the present invention whether emulsion preconcentrates or emulsions may be employed for administration in any appropriate manner and form; e.g. orally, as liquids or granules or in unit dosage form, for example in hard or soft gelatin encapsulated form, parenterally or topically; e.g. for application to the skin; for example in the form of a cream, paste, lotion, gel, ointment, poultice, cataplasm, plaster, dermal patch, powder, topically applicable spray, or the like, or for ophthalmic application; for example in the form of an eye-drop, lotion or gel formulation. Readily flowable forms may also be employed; e.g. for intralesional injection for the treatment of psoriasis, or may be administered rectally. Compositions in accordance with the invention are, however, primarily intended for oral or topical application, including application to the skin or eyes.

The relative proportion of drug and other ingredients in the compositions of the invention will, of course, vary considerably depending on the particular type of composition concerned; e.g. whether it is an emulsion preconcentrate or emulsion, the route of administration, and so forth. The relative proportions will also vary, depending on the identity and particular function of ingredients in the composition; for example, in the case of a surfactant component of an emulsion preconcentrate, on whether this is employed as a surfactant only or both a surfactant and a co-solvent. The relative proportions will also vary depending on the particular ingredients employed and the desired physical characteristics of the product composition, e.g. in the case of a composition for topical use, whether this is to be a free flowing liquid or a paste. Determination of workable proportions in any particular instance will generally be within the capability of persons skilled in the art. All indicated proportions and relative weight ranges described herein are accordingly to be understood as being examples and not as not limiting the invention in its broadest aspect.

Compositions for topical use suitably comprise one or more carriers or diluents and/or other ingredients (e.g. thickening agents, emulsifying agents, preserving agents, moisturising agents, colourants and so forth) providing a suitable carrier.

Selection of excipients for the preparation of such formulations will, of course, be determined by the type of formulation desired as well as the particular condition to be treated, the area to be treated, and the effect desired. Some conditions will more suitably be treated with hydrophobic, e.g. fat-based compositions, for example compositions in accordance with the invention comprising a petrolatum based ointment or cream as carrier medium. In contrast, compositions for use in the treatment of some conditions will more appropriately be treated with more hydrophilic compositions, e.g. compositions in accordance with the invention in the form of an oil-in-water emulsion or gel.

Especially preferred compositions are compositions in which an emulsion preconcentrate is dispersed in a suitable pharmaceutically acceptable diluent or carrier. Compositions as aforesaid may take the form of a water-free or substantially water-free emulsion, i.e., comprise less than 10%, preferably less than 5%, most preferably less than 1% water.

Suitable carrier components include, for example:

Solid hydrocarbons, for example petroleum jellies, e.g. white petrolatum, ceresin and solid paraffins, as well as waxes including animal, vegetable and synthetic waxes such as, for example, spermaceti, carnauba and bees wax;

Liquid hydrocarbons, e.g. liquid paraffins and fatty acid esters such as isopropylmyristate and cetyl palmitate;

Non-volatile silicones including silicone oils and pastes, and silicone-polyalkyleneoxide co-polymers for example such as known and commercially available under the trade name Piroethicon.

Such carrier components will suitably be present in the compositions in an amount up to about 80%, e.g., from about 5 to about 70%, preferably from about 25 to about 60% by weight based on the total weight of the composition.

By use of suitable individual carrier ingredients or mixtures thereof, emulsions may be obtained in liquid or semi-solid form depending on, e.g., desired requirements for topical application.

Compositions for topical use may further comprise one or more consistency promoting agents, for example microcrystalline waxes, vegetable oils such as olive oils, corn oils and kernel oils, and vegetable oil derivatives including hydrogenated vegetable oils and vegetable oil partial-glycerides, e.g. in an amount of from about 0.1 to about 10%, preferably from about 1 to about 5% weight based on the total weight of the composition.

Such compositions will also suitably contain other ingredients which may include an anti-oxidant, and anti-bacterial agent, a stabilizer, and a skin penetration enhancer.

In addition to the foregoing the present invention also provides a process for the production of a pharmaceutical composition hereinbefore defined which process comprises bringing the individual components thereof into intimate admixture and, when required compounding the obtained composition in unit dosage form, for example filling said composition into soft or hard gelatin capsules, or dispersing the composition in a carrier which may include water.

BEST MODE OF CARRYING OUT THE INVENTION

Preferred alcohols for use as principal solvent for the drug are alcohols having a boiling point above 150° C., a melting point under 40°, and a solubility in water of under 5 g per 100 g at 20° C. Especially preferred alcohols are 1octyl, 2-octyl, 1-decyl, 1-dodecyl, 1-tetradecyl, benzyl and phenethyl alcohols.

Where two or more alcohols are to be used, a preferred combination is one selected from 1-octyl, 2-octyl, 1-decyl, 1-dodecyl, and 1-tetradecyl alcohols and another selected from benzyl and phenethyl.

Preferred surfactants are reaction products of natural or hydrogenated vegetable oils and ethylene glycol; i.e., polyoxethylene glycolated natural or hydrogenated vegetable oils.

Especially preferred surfactants are polyoxyethylene glycolated natural or hydrogenated castor oils, including those designated in the United States Pharmacopoeia and National Formulary as Polyoxyl and Polyoxyl 40 Hydrogenated Castor Oil.

The invention will be more fully understood by the following examples which are illustrative but not limiting of compositions in accordance with the present invention.

EXAMPLE 1

The following were placed in a test tube:

cyclosporine 1.04 g;

1-octyl alcohol 2.5 g; and polyoxyl 40 hydrogenated castor oil 2.0 g.

Upon agitation, a clear solution was gradually formed.

EXAMPLE 2

The following were placed in a test tube:

cyclosporine 1.04 g;

1-octyl alcohol 2.5 g; and polyoxyl 35 castor oil 1.0 g.

Upon agitation, a clear solution was gradually formed.

EXAMPLE 3

The following were placed in a test tube, after the 1-dodecyl was warmed to above 25° C.:

cyclosporine 1.04 g;

1-dodecyl alcohol 2.5 g; and polyoxyl 35 castor oil 1.0 g.

Upon agitation, a clear solution was gradually formed.

EXAMPLE 4

The following were placed in a test tube:

cyclosporine 1.04 g;

1-octyl alcohol 1.0 g;
benzyl alcohol 0.25 g; and
polyoxyl 35 castor oil 1.0 g.
Upon agitation, a clear solution was gradually formed.

EXAMPLE 5

The following were placed in a test tube:
cyclosporine 1.04 g;
1-decyl alcohol 1.0 g;
benzyl alcohol 0.25 g; and
polyoxyl 35 castor oil 1.0 g.
Upon agitation a clear solution was gradually formed.

EXAMPLE 6

The following were placed in a test tube, after the 1-dodecyl alcohol was warmed to about 25° C.:
cyclosporine 5.20 g;
1-dodecyl alcohol 5.00 g;
benzyl alcohol 1.20 g; and
polyoxyl 35 castor oil 5.00 g.
Upon agitation a clear solution was gradually formed.

EXAMPLE 7

The following were placed in a test tube, after the 1-dodecyl alcohol was warmed to about 25° C.:
cyclosporine 1.04 g;
1-dodecyl alcohol 1.0 g;
phenethyl alcohol 0.25 g; and
polyoxyl 35 castor oil 1.0 g.
Upon agitation a clear solution was gradually formed.

In the case of each of examples 1 to 7, the solution formed was readily dispersible in water to form an emulsion without precipitation of the cyclosporine.

The solution of example 6 was filled into hard gelatin capsules. The absorption was compared in human volunteers to that of Sandimmure (registered trademark) capsules which is the leading brand in the world market and made in accordance with U.S. Pat. No. 4,388,307. This was done by performing a comparative bioavailability study in which capsules were ingested by human volunteers, blood samples were drawn and cyclosporine levels were measured. It was found that the extent of absorption of the composition of example 6 was substantially greater than that of Sandimmune (registered trademark).

The solutions of each of examples 1 to 7 are directly useable as drops for oral ingestion or as a liquid for opthalmic or topical use.

Alternatively, they may be further processed in various ways previously described, including, for example, their incorporation into gelatin capsules or tablets for oral ingestion, or into emulsions and various other forms for oral or topical use.

For example, they may be incorporated into a cream, ointment, gel or the like by combination with further additives, e.g., thickening agents, paraffins, etc. as hereinbefore described.

The aforesaid examples use cyclosporine as the drug. However, similar compositions can be prepared using other drugs that are soluble in alcohols or in solvent systems containing alcohols and surfactants.

INDUSTRIAL APPLICABILITY

From the foregoing description it will be apparent that in the present invention there is provided an improved pharmaceutical composition which permits the more efficient administration and absorption of hydrophobic drugs.

I claim:

1. A water-dispersible pharmaceutical composition comprising a monocyclic non-polar peptide dissolved in a solvent system, wherein the solvent system comprises at least one alcohol selected from saturated alkyl mono-alcohols having from 6 to 16 carbon atoms per molecule, a boiling point above 100° C. and a solubility in water of less than 10 g per 100 g at 20° C., and said solvent system further comprises at least one pharmaceutically-acceptable surfactant.

2. A composition according to claim 1 wherein said alcohol has from 8 to 14 carbon atoms per molecule.

3. A composition according to claim 1 wherein said solvent system comprises an alcohol selected from 1-octyl, 2-octyl, 1-decyl, and 1dodecyl alcohols.

4. A composition according to claim 1 wherein said monocyclic non-polar peptide is a cyclosporin.

5. A composition according to claim 1 wherein said monocyclic non-polar peptide is cyclosporine.

6. A composition according to claim 5 wherein said solvent system comprises 1-decyl alcohol or 1-dodecyl alcohol.

7. A composition according to claim 1 wherein said solvent system further comprises benzyl or phenethyl alcohol.

8. A composition according to claim 1 wherein said surfactant is a polyoxyethylene glycolated natural or hydrogenated vegetable oil.

9. A composition according to claim 1 wherein said surfactant is a polyoxyethylene glycolated natural or hydrogenated castor oil.

10. A composition according to claim 1 which is dispersed in a carrier.

11. A composition according to claim 10 wherein the carrier is water or contains water.

12. A composition according to claim 1 in a liquid form.

13. A composition according to claim 1 contained within a gelatin capsule.

14. A composition according to claim 1 adapted for oral administration.

15. A composition according to claim 1 adapted for topical or ophthalmic administration.

16. A composition according to claim 1 adapted for parenteral administration.

17. The composition according to claim 1 wherein said composition further comprises a non-saturated alkyl mono-alcohol having at least 6 carbon atoms per molecule wherein the total amount by weight of saturated alkyl mono-alcohols present in said composition is greater than the total amount by weight of said non-saturated alkyl mono-alcohol present in said composition.

* * * * *